(12) United States Patent
Bennett et al.

(10) Patent No.: US 9,157,081 B2
(45) Date of Patent: Oct. 13, 2015

(54) CHIMERIC OLIGOMERIC COMPOUNDS FOR MODULATION OF SPLICING

(71) Applicants: Isis Pharmaceuticals, Inc., Carlsbad, CA (US); Sarepta Therapeutics, Cambridge, MA (US)

(72) Inventors: C. Frank Bennett, Carlsbad, CA (US); Nicholas M. Dean, Olivenhain, CA (US); Ryszard M. Kole, Chapel Hill, NC (US); Casey C. Kopczynski, Chapel Hill, NC (US)

(73) Assignees: Isis Pharmaceuticals, Inc., Carlsbad, CA (US); Sarepta Therapeutics, Cambridge, MA (US)

( * ) Notice: Subject to any disclaimer, the term of this patent is extended or adjusted under 35 U.S.C. 154(b) by 0 days.

(21) Appl. No.: 13/934,489

(22) Filed: Jul. 3, 2013

(65) Prior Publication Data
US 2014/0005374 A1 Jan. 2, 2014

Related U.S. Application Data

(63) Continuation of application No. 12/065,250, filed as application No. PCT/US2006/034308 on Aug. 29, 2006, now Pat. No. 8,501,703.

(60) Provisional application No. 60/712,674, filed on Aug. 30, 2005.

(51) Int. Cl.
*C07H 21/04* (2006.01)
*C12N 15/113* (2010.01)
*C12N 15/11* (2006.01)

(52) U.S. Cl.
CPC ............ *C12N 15/113* (2013.01); *C12N 15/111* (2013.01); *C12N 15/1135* (2013.01); *C12N 2310/321* (2013.01); *C12N 2310/322* (2013.01); *C12N 2310/346* (2013.01); *C12N 2320/33* (2013.01)

(58) Field of Classification Search
None
See application file for complete search history.

(56) References Cited

U.S. PATENT DOCUMENTS

| | | | |
|---|---|---|---|
| 5,627,274 A | 5/1997 | Kole et al. |
| 5,665,593 A | 9/1997 | Kole et al. |
| 5,916,808 A | 6/1999 | Kole et al. |
| 5,976,879 A | 11/1999 | Kole et al. |
| 6,172,216 B1 | 1/2001 | Bennett et al. |
| 6,210,892 B1 | 4/2001 | Bennett et al. |
| 6,214,986 B1 | 4/2001 | Bennett et al. |
| 2002/0049173 A1 | 4/2002 | Bennett et al. |
| 2003/0036519 A1 | 2/2003 | Kole et al. |
| 2003/0083477 A1 | 5/2003 | Arrow et al. |
| 2003/0114411 A1 | 6/2003 | Kole et al. |
| 2005/0054836 A1 | 3/2005 | Krainer et al. |
| 2005/0074801 A1 | 4/2005 | Monia et al. |
| 2005/0142535 A1 | 6/2005 | Damha et al. |
| 2005/0142581 A1 | 6/2005 | Griffey et al. |

FOREIGN PATENT DOCUMENTS

| | | |
|---|---|---|
| WO | WO 94/26887 | 11/1994 |
| WO | WO 02/38738 | 5/2002 |
| WO | WO 02/44321 | 6/2002 |

OTHER PUBLICATIONS

Caplen, "RNAi as a Gene Therapy Approach" Expert Opinion Biol. Therapy (2003) 3(4):575-586.
Crooke et al., "Kinetic Characteristics of *Escherichia coli* Rnase H1: Cleavage of Various Antisense Oligonucleotide-RNA Duplexes" Biochemical Journal (1995) 312(2):599-608.
Dominski & Kole, "Restoration of correct splicing in thalassemic pre-mRNA by antisense oligonucleotides" PNAS (1993) 90:8673-8677.
Dunckley et al., "Modification of splicing in the dystrophin gene in cultured Mdx muscle cells by antisense oligonucleotides" Human Mol. Genetics (1995) 50):1083-1090.
Dunckley et al., "Modulation of Splicing in the DMD Gene by Antisense Oligoribonucleotides" Nucleosides & Nucleotides (1997) 16(7-9):1665-1668.
Friedman et al., "Correction of Aberrant Splicing of the Cystic Fibrosis Transmembrane Conductance Regulator (CFTR) Gene by Antisense Oligonucleotides" J. Biol. Chem. (1999) 274(51):36193-36199.
Jen et al., "Suppresion of Gene by Targeted Disruption of Messenger RNA: Available Options and Current Strategies" Stem Cells (2000) 18:307-319.
Kole, "Modification of pre-mRNA splicing by antisense oligonucleotides" Acta Biochimica Polonica (1997) 44(2):231-238.
Kurreck, "Antisense technologies: Improvement through novel chemical modifications" Eur. J. Biochem. (2003) 270:1628-1644.
Lacerra et al., "Restoration of hemoglobin A synthesis in erythroid cells from peripheral blood of thalassemic patients" PNAS (2000) 97:9591-9596.
Monia et al., "Evaluation of 2'-Modified Oligonucleotides Containing 2'-Deoxy Gaps as Antisense Inhibitors of Gene Expression" Journal of Biological Chemistry (1993) 268(19):14514-14522.
Novina et al., "The RNAi Revolution" Nature (2004) 430:161-164.
Sazani et al., "Therapeutic potential of antisense oligonucleotides as modulators of alternative splicing" J. Clin. Invest. (2003) 112:481-486.
Sierakowska et al., "Restoration of Beta-Globin Gene Expression in Mammalian Cells by Antisense Oligonucleotides that Modify the Aberrant Splicing Patterns of Thalassemic Pre-mRNAs" Nucleosides & Nucleotides (1997) 16(7-9):1173-1182.

(Continued)

*Primary Examiner* — Kimberly Chong
(74) *Attorney, Agent, or Firm* — Knobbe, Martens, Olson & Bear, LLP

(57) ABSTRACT

Disclosed herein are compounds, compositions and methods for modulating splicing of a selected target mRNA. Further provided are uses of the disclosed compounds and compositions in the manufacture of a medicament for treatment of diseases and disorders. Methods of enhancing cellular uptake, modulating tissue distribution and enhancing pharmacological activity of RNase H-independent antisense oligonucleotides are also provided.

6 Claims, No Drawings

(56) References Cited

OTHER PUBLICATIONS

Sierakowska et al., "Repair of thalassemic human beta-globin mRNA in mammalian cells by antisense oligonucleotides" PNAS (1996) 93:12840-12844.

Taylor et al., "Induction of endogenous Bcl-xS through the control of Bcl-x pre-mRNA splicing by antisense oligonucleotides" Nat. Biotechnol. (1999) 17:1097-1100.

Vickers et al., "Efficient Reduction of Target RNAs by siRNA and Rnase H-dependent Antisense" Journal of Biological Chemistry (2003) 278(9):7108-7118.

Wang & Marini, "Antisense Oligodeoxynucleotides Selectively Suppress Expression of the Mutant alpha2(I) Collagen Allele in Type IV Osteogenesis Imperfecta Fibroblasts" J. Clin. Invest. (1996) 97:448-454.

Wilton et al., "Specific removal of the nonsense mutation from the mdx dystrophin mRNA using antisense oligonucleotides" Neuromuscul. Discord (1999) 9:330-338.

Supplementary European Search Report for application EP 06802842.2 dated Dec. 29, 2009.

International Search Report for application PCT/US06/34308 dated Jul. 31, 2007.

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Oligomeric compound

<400> SEQUENCE: 1
tggttcttac ccagccgccg                    20

<210> SEQ ID NO 2
<211> LENGTH: 20
<212> TYPE: DNA
<213> ORGANISM: Artificial Sequence
<220> FEATURE:
<223> OTHER INFORMATION: Oligomeric compound

<400> SEQUENCE: 2
gttattcttt agaatggtgc                    20

<210> SEQ ID NO 3
<211> LENGTH: 20
<212> TYPE: DNA
<213> ORGANISM: Artificial Sequence
<220> FEATURE:
<223> OTHER INFORMATION: Oligomeric compound

<400> SEQUENCE: 3
tgctattacc ttaacccaga                    20

CHIMERIC OLIGOMERIC COMPOUNDS FOR MODULATION OF SPLICING

CROSS-REFERENCE TO RELATED APPLICATIONS

This application is a continuation of U.S. application Ser. No. 12/065,250, filed Feb. 28, 2008, which is a U.S. National Phase filing under 35 U.S.C. §371 claiming priority to International Serial No. PCT/US2006/034308 filed Aug. 29, 2006, which claims priority to U.S. Provisional Application 60/712,674, filed Aug. 30, 2005, each of which is incorporated herein by reference in its entirety.

INCORPORATION OF SEQUENCE LISTING

A copy of the sequence listing in both a paper and a computer-readable form is provided herewith and hereby incorporated by reference. The computer readable form is provided on diskette containing the file named CORE0059USC1SEQ.txt, which was created on Jun. 27, 2013.

BACKGROUND

Newly synthesized eukaryotic mRNA molecules, also known as primary transcripts or pre-mRNA, made in the nucleus, are processed before or during transport to the cytoplasm for translation. Processing of the pre-mRNAs includes addition of a 5' methylated cap and an approximately 200-250 base poly(A) tail to the 3' end of the transcript.

The next step in mRNA processing is splicing of the pre-mRNA, which occurs in the maturation of 90-95% of mammalian mRNAs. Introns (or intervening sequences) are regions of a primary transcript (or the DNA encoding it) that are not included in the coding sequence of the mature mRNA. Exons are regions of a primary transcript that remain in the mature mRNA when it reaches the cytoplasm. The exons are spliced together to form the mature mRNA sequence. Splice junctions are also referred to as splice sites with the 5' side of the junction often called the "5' splice site," or "splice donor site" and the 3' side the "3' splice site" or "splice acceptor site." In splicing, the 3' end of an upstream exon is joined to the 5' end of the downstream exon. Thus the unspliced RNA (or pre-mRNA) has an exon/intron junction at the 5' end of an intron and an intron/exon junction at the 3' end of an intron. After the intron is removed, the exons are contiguous at what is sometimes referred to as the exon/exon junction or boundary in the mature mRNA. Cryptic splice sites are those which are less often used but may be used when the usual splice site is blocked or unavailable. Alternative splicing, defined as the splicing together of different combinations of exons, often results in multiple mRNA transcripts from a single gene.

Up to 50% of human genetic diseases resulting from a point mutation are caused by aberrant splicing. Such point mutations can either disrupt a current splice site or create a new splice site, resulting in mRNA transcripts comprised of a different combination of exons or with deletions in exons. Point mutations also can result in activation of a cryptic splice site or disrupt regulatory cis elements (i.e. splicing enhancers or silencers) (Cartegni et al., Nat. Rev. Genet., 2002, 3, 285-298; Krawczak et al., Hum. Genet., 1992, 90, 41-54).

Antisense oligonucleotides have been used to target mutations that lead to aberrant splicing in several genetic diseases in order to redirect splicing to give a desired splice product (Kole, Acta Biochimica Polonica, 1997, 44, 231-238). Phosphorothioate 2'-O-methyl oligoribonucleotides have been used to target the aberrant 5' splice site of the mutant β-globin gene found in patients with β-thalassemia, a genetic blood disorder. Aberrant splicing of mutant β-globin mRNA was blocked and normal splicing was restored in vitro in vector constructs containing thalassemic human β-globin pre-mRNAs using 2'-O-methyl-ribo-oligonucleotides targeted to the branch point sequence in the first intron of the mutant human β-globin pre mRNAs (Dominski and Kole, Proc. Natl. Acad. Sci. USA, 1993, 90, 8673-8677). Oligonucleotides targeted to the aberrant β-globin splice site suppressed aberrant splicing and at least partially restored correct splicing in HeLa cells expressing the mutant transcript (Sierakowska et al., Nucleosides & Nucleotides, 1997, 16,1173-1182; Sierakowska et al., Proc. Natl. Acad. Sci. USA, 1996, 93, 12840-44). U.S. Pat. No. 5,627,274 and WO 94/26887 disclose compositions and methods for combating aberrant splicing in a pre-mRNA molecule containing a mutation using antisense oligonucleotides which do not activate RNAse H.

Modulation of mutant dystrophin splicing with 2'-O-methyl oligoribonucleotides has been reported both in vitro and in vivo. In dystrophin Kobe, a 52-base pair deletion mutation causes exon 19 to be skipped during splicing. An in vitro minigene splicing system was used to show that a 31-mer 2'-O-methyl oligoribonucleotide complementary to the 5' half of the deleted sequence in dystrophin Kobe exon 19 inhibited splicing of wild-type pre-mRNA. The same oligonucleotide was used to induce exon skipping from the native dystrophin gene transcript in human cultured lymphoblastoid cells (Takeshima et al., J. Clin. Invest., 1995, 95, 515-520).

Dunckley et al. (Nucleosides & Nucleotides, 1997, 16, 1665-1668) describes in vitro constructs for analysis of splicing around exon 23 of mutated dystrophin in the mdx mouse mutant, a model for Duchenne muscular dystrophy. 2'-O-methyl oligoribonucleotides were used to correct dystrophin deficiency in myoblasts from the mdx mouse. An antisense oligonucleotide targeted to the 3' splice site of murine dystrophin intron 22 caused skipping of the mutant exon and created a novel in-frame dystrophin transcript with a novel internal deletion. This mutated dystrophin was expressed in 1-2% of antisense treated mdx myotubes. The use of other oligonucleotide modifications, such as 2'-O-methoxyethyl phosphodiesters, is disclosed (Dunckley et al. Human Mol. Genetics, 1998, 5, 1083-90).

Phosphorothioate oligodeoxynucleotides have been used to selectively suppress the expression of a mutant α2(I) collagen allele in fibroblasts from a patient with osteogenesis imperfecta, in which a point mutation in the splice donor site produces mRNA with exon 16 deleted. The oligonucleotides were targeted either to the point mutation in the pre-mRNA or to the defectively spliced transcript. In both cases mutant mRNA was decreased by half with the normal transcript decreased by 20% (Wang and Marini, J. Clin Invest., 1996, 97, 448-454).

Antisense compounds have been used to block cryptic splice sites to restore normal splicing of HBB (β-globin) and CFTR genes in cell lines derived from β-thalassemia or cystic fibrosis patients, respectively (Lacerra et al., Proc. Natl. Acad. Sci. USA, 2000, 97, 9591-9596; Friedman et al., J. Biol. Chem., 1999, 274, 36193-36199). Antisense compounds have also been used to alter the ratio of the long and short forms of Bcl-x pre-mRNA (U.S. Pat. No. 6,172,216; U.S. Pat. No. 6,214,986; Taylor et al., Nat. Biotechnol. 1999, 17, 1097-1100) or to force skipping of specific exons containing premature termination codons (Wilton et al., Neuromuscul. Disord., 1999, 9, 330-338).

Kole et al. (WO 94/26887 and U.S. Pat. Nos. 5,627,274; 5,916,808; 5,976,879; and 5,665,593) disclose methods of combating aberrant splicing using modified antisense oligonucleotides which do not activate RNase H.

U.S. Pre-Grant Publications 2003-0114411 and 2003-0036519 discuss antisense oligonucleotides conjugated to a nuclear localization element for use in upregulating expression of a cellular protein, which is encoded by a DNA comprising a mutation which results in aberrant splicing of the pre-mRNA.

A method of controlling the behavior of a cell through modulation of the processing of an mRNA target by contacting the cell with an antisense compound acting via a non-cleavage event is disclosed in U.S. Pat. No. 6,210,892 and U.S. Pre-Grant Publication 2002-0049173.

PCT Publication WO 02/38738 and U.S. Pre-Grant Publication 2005-0054836 disclose chimeric molecules comprising a base-pairing segment which specifically binds to a single-stranded target nucleic acid, and a moiety which modulates splicing or translation. Further disclosed are methods of using the chimeric molecules for modulating splicing or translation of a target nucleic acid molecule.

U.S. Pre-Grant Publication 2005-0074801 discloses chimeric oligomeric compounds with regions of nucleosides that are DNA-like and regions of nucleosides that are RNA-like.

Although a number of antisense compounds that are capable of modulating splicing of a target gene in vitro have been reported, there remains a need to identify compounds suitable for therapeutic use in vivo. In order for an antisense oligonucleotide to achieve therapeutic success, oligonucleotide chemistry must allow for adequate cellular uptake (Kurreck, J. (2003) Eur. J. Biochem. 270:1628-1644). Splicing oligonucleotides have traditionally been comprised of uniform modifications that render the oligonucleotide RNA-like, and thus resistant to cleavage by RNase H, which is critical to achieve modulation of splicing. Provided herein are antisense compounds for modulation of splicing. The disclosed compounds are chimeric, with regions of RNA-like and DNA-like chemistry. Despite regions of DNA-like chemistry, the chimeric compounds are RNase H-resistant and effectively modulate splicing of target mRNA in vitro and in vivo. Furthermore, the disclosed chimeric oligomeric compounds show enhanced cellular uptake and greater pharmacologic activity compared with uniformly modified oligonucleotides.

SUMMARY

Provided herein are methods of modulating splicing of a selected target mRNA in cells or tissues by contacting the cells or tissues with a chimeric oligomeric compound targeted to the selected mRNA, comprising a modified sugar moiety at the 5'-most nucleoside; a modified sugar moiety at the 3'-most nucleoside; internal nucleosides comprising 2, 3, 4 or 5 separate regions of 2'-deoxyribonucleosides; and at least one nucleoside with a modified sugar moiety separating each region of 2'-deoxyribonucleosides. The compounds provided herein have up to 4 nucleosides in each region of 2'-deoxyribonucleosides. In one embodiment, each region of 2'-deoxyribonucleosides consists of either 2 or 3 nucleosides. In one preferred embodiment, the compounds comprise 3 separate regions of 2'-deoxyribonucleosides. In another preferred embodiment, the compounds comprise 4 separate regions of 2'-deoxyribonucleosides. In one aspect of the methods, the 5' end, the 3' end, or both the 5' and 3' ends of the compounds consist of 2, 3, 4 or 5 modified sugar residues.

In one embodiment, the sugar modifications are selected from the group consisting of 2'-O-methoxyethyl, 2'-fluoro, 2'-dimethylaminooxyethoxy, 2'-dimethylaminoethoxyethoxy, 2'-guanidinium, 2'-O-guanidinium ethyl, 2'-carbamate, 2'-aminooxy, 2'-acetamido and locked nucleic acid. In one preferred embodiment, the sugar modification is 2'-O-methoxyethyl. In further embodiments, the chimeric oligomeric compounds are 13 to 80 nucleobases in length, 13 to 50 nucleobases in length, 13 to 30 nucleobases in length, 20 to 30 nucleobases in length, 15 to 25 nucleobases in length or 20 nucleobases in length. In other embodiments, the cells or tissues are derived from adipose or liver. Contemplated herein are chimeric oligomeric compounds which are targeted to a splice site of a target mRNA. Splice sites include aberrant and cryptic splice sites.

Also provided are chimeric RNase H-independent antisense compounds targeted to a selected target mRNA. The RNase H-independent antisense compounds comprise a modified sugar moiety at the 5'-most nucleoside; a modified sugar moiety at the 3'-most nucleoside; internal nucleosides comprising 2, 3, 4 or 5 separate regions of 2'-deoxyribonucleosides; and at least one nucleoside with a modified sugar moiety separating each region of 2'-deoxyribonucleosides. The chimeric RNase H-independent compounds provided herein have up to 4 nucleotides in each region of 2'-deoxyribonucleosides. In one embodiment, each region of 2'-deoxyribonucleosides consists of either 2 or 3 nucleosides. In one preferred embodiment, the compounds comprise 3 separate regions of 2'-deoxyribonucleosides. In another preferred embodiment, the compounds comprise 4 separate regions of 2'-deoxyribonucleosides. In one aspect of the methods, the 5' end, the 3' end, or both the 5' and 3' ends of the compounds consist of 2, 3, 4 or 5 modified sugar residues.

In one embodiment, the sugar modifications of the chimeric RNase H-independent compounds are selected from the group consisting of 2'-O-methoxyethyl, 2'-fluoro, 2'-dimethylaminooxyethoxy, 2'-dimethylaminoethoxyethoxy, 2'-guanidinium, 2'-O-guanidinium ethyl, 2'-carbamate, 2'-aminooxy, 2'-acetamido and locked nucleic acid. In one preferred embodiment, the sugar modification is 2'-O-methoxyethyl. In one aspect, cellular uptake of the chimeric compounds is enhanced compared with a compound of the same sequence with modified sugar residues at each position. In another aspect, the chimeric compounds modulate splicing of a selected target mRNA. In one embodiment, the chimeric compounds that modulate splicing are specifically hybridizable with a splice site of the selected target mRNA. In further embodiments, the splice site is an aberrant splice site or a cryptic splice site.

Further provided herein are methods of enhancing cellular uptake, methods of enhancing pharmacologic activity and methods of modulating tissue distribution of RNase H-independent antisense oligonucleotides with uniformly modified sugar residues, comprising substituting selected modified sugar residues with 2'-deoxyribose sugar residues such that the antisense oligonucleotide comprises a modified sugar moiety at the 5'-most nucleoside; a modified sugar moiety at the 3'-most nucleoside; internal nucleosides comprising 2, 3, 4 or 5 separate regions of 2'-deoxyribonucleosides; and at least one nucleoside with a modified sugar moiety separating each region of 2'-deoxyribonucleosides. The antisense oligonucleotides provided herein have up to 4 nucleosides in each region of 2'-deoxyribonucleosides. In one embodiment, the sugar modification of the RNase H-independent antisense oligonucleotide is selected from the group consisting of 2'-O-methoxyethyl, 2'-fluoro, 2'-dimethylaminooxyethoxy, 2'-dimethylaminoethoxyethoxy, 2'-guanidinium, 2'-O-guanidinium ethyl, 2'-carbamate, 2'-aminooxy, 2'-acetamido and locked nucleic acid. In one preferred embodiment, the sugar modification is 2'-O-(2-methoxyethyl). Contemplated herein are methods of enhancing cellular uptake in vitro, ex vivo and in vivo. Further contemplated are methods of modulating tissue distribution such that there is an increase in oligonucleotide concentration in adipose tissue or in the liver.

Also provided are chimeric RNase H-independent antisense compounds for use in therapy. Use of a chimeric RNase H-independent antisense compound for the preparation of a medicament for modulation of splicing of a selected mRNA in cells or tissues is also provided.

DETAILED DESCRIPTION

Disclosed herein are chimeric oligomeric compounds for modulation of splicing of a selected target mRNA. Modulation of splicing has previously been achieved using uniformly modified oligomeric compounds (i.e. oligonucleotides with the same chemical modification at each nucleotide position), wherein the modifications render the compounds "RNA-like" to prevent cleavage by RNase H. Such modified compounds modulate splicing through an occupancy-based antisense mechanism. Provided herein are chimeric oligomeric compounds with at least one nucleoside with a modified sugar residue at the 5' and 3' ends and internal regions of 2'-deoxyribonucleosides, each region being separated by at least one nucleoside with a modified sugar residue. The internal regions of 2'-deoxyribonucleosides, which are the "DNA-like" regions, can be up to 4 nucleosides in length. Despite regions of "DNA-like" chemistry, the chimeric oligomeric compounds disclosed herein are capable of modulating target mRNA splicing without target degradation. Such chimeric oligomeric compounds exhibit enhanced cellular uptake and greater pharmacologic activity.

Further provided are RNase H-independent antisense compounds in which selected modified sugar residues are replaced with 2'-deoxyribose sugar residues. Uses of the chimeric antisense compounds include modulation of splicing of a selected target mRNA, enhancing cellular uptake of RNase H-independent oligonucleotides, enhancing pharmacologic activity of RNase H-independent oligonucleotides and modulating tissue distribution of RNase H-independent oligonucleotides.

The principle behind antisense technology is that an antisense compound, which hybridizes to a target nucleic acid, modulates gene expression activities such as transcription, splicing or translation. This sequence specificity makes antisense compounds extremely attractive as tools for target validation and gene functionalization, as well as therapeutics to selectively modulate the expression of genes or gene products involved in disease.

As used herein, "antisense mechanisms" are all those involving hybridization of a compound with target nucleic acid, wherein the outcome or effect of the hybridization is either target degradation or target occupancy with concomitant stalling of the cellular machinery involving, for example, transcription or splicing. Target degradation can include an RNase H, which is a cellular endonuclease which cleaves the RNA strand of an RNA:DNA duplex. It is known in the art that single-stranded antisense compounds which are "DNA-like" elicit cleavage by RNAse H. Occupancy-based antisense mechanisms, whereby antisense compounds hybridize yet do not elicit cleavage of the target, include inhibition of translation, modulation of splicing, modulation of poly(A) site selection and disruption of regulatory RNA structure. "RNA-like" antisense compounds for use in occupancy-based antisense mechanisms are known in the art.

As used herein, oligomeric compounds (e.g., antisense oligonucleotides) that are "RNase H-independent" are those compounds which do not elicit cleavage by RNase H when hybridized to a target nucleic acid. RNase H-independent oligomeric compounds modulate gene expression, such as splicing, by a target occupancy-based mechanism.

As used herein, "uniformly modified" refers to an oligomeric compound, an antisense oligonucleotide, or a region of nucleotides which comprise nucleotides with identical chemical modifications throughout the compound, oligonucleotide or region.

As used herein, a "chimeric oligomeric compound" is a compound containing two or more chemically distinct regions, each comprising at least one monomer unit (i.e., a nucleotide in the case of an oligonucleotide compound). In the context of the present disclosure, a "chimeric RNase H-independent antisense compound" is an antisense compound with at least two chemically distinct regions, but which is not susceptible to cleavage by RNase H when hybridized to a target nucleic acid.

As used herein, a "nucleoside" is a base-sugar combination and "nucleotides" are nucleosides that further include a phosphate group covalently linked to the sugar portion of the nucleoside.

As used herein, a nucleoside with a modified sugar residue is any nucleoside wherein the 2'-deoxyribose sugar has been substituted with a chemically modified sugar moiety. In the context of the present disclosure, the chemically modified sugar moieties include, but are not limited to, 2'-O-methoxyethyl, 2'-fluoro, 2'-dimethylaminooxyethoxy, 2'-dimethylaminoethoxyethoxy, 2'-guanidinium, 2'-O-guanidinium ethyl, 2'-carbamate, 2'-aminooxy, 2'-acetamido and locked nucleic acid.

As used herein, "targeting" or "targeted to" refer to the process of designing an oligomeric compound such that the compound hybridizes with a selected nucleic acid molecule or region of a nucleic acid molecule.

As used herein, "target mRNA" refers to the nucleic acid molecule to which the oligomeric compounds provided herein are designed to hybridize. In the context of the present disclosure, target mRNA is unspliced mRNA, or pre-mRNA.

As used herein, "hybridization" means the pairing of complementary strands of oligomeric compounds. In the context of the present disclosure, an oligomeric compound is specifically hybridizable when there is a sufficient degree of complementarity to avoid non-specific binding of the oligomeric compound to non-target nucleic acid sequences. One of skill in the art will be able to determine when an oligomeric compound is specifically hybridizable.

As used herein, "modulation of splicing" refers to altering the processing of a pre-mRNA transcript such that there is an increase or decrease of one or more splice products, or a change in the ratio of two or more splice products. Modulation of splicing can also refer to altering the processing of a pre-mRNA transcript such that a spliced mRNA molecule contains either a different combination of exons as a result of exon skipping or exon inclusion, a deletion in one or more exons, or additional sequence not normally found in the spliced mRNA (e.g., intron sequence).

As used herein, "splice site" refers to the junction between an exon and an intron in a pre-mRNA (unspliced RNA) molecule (also known as a "splice junction"). A "cryptic splice site" is a splice site that is not typically used but may be used when the usual splice site is blocked or unavailable or when a mutation causes a normally dormant site to become an active splice site. An "aberrant splice site" is a splice site that results from a mutation in the native DNA and mRNA. In the context of the present disclosure, an oligomeric compound "targeted to a splice site" refers to a compound that hybridizes with at least a portion of a region of nucleic acid encoding a splice site or a compound that hybridizes with an intron or exon in proximity to a splice site, such that splicing of the mRNA is modulated.

In the context of the present disclosure, "cellular uptake" refers to delivery and internalization of oligomeric compounds into cells. The oligomeric compounds can be internalized, for example, by cells grown in culture (in vitro), cells harvested from an animal (ex vivo) or by tissues following administration to an animal (in vivo).

Provided herein are methods of modulating splicing of a selected target mRNA in cells or tissues whereby the cells or tissues are contacted with a chimeric antisense compound comprising a modified sugar moiety at the 5'-most nucleoside; a modified sugar moiety at the 3'-most nucleoside; internal nucleosides comprising 2, 3, 4 or 5 separate regions of 2'-deoxyribonucleosides; and at least one nucleoside with a modified sugar moiety separating each region of 2'-deoxyribonucleosides.

In one embodiment, the sugar modification is selected from 2'-O-methoxyethyl, 2'-fluoro, 2'-dimethylaminooxyethoxy, 2'-dimethylaminoethoxyethoxy, 2'-guanidinium, 2'-O-guanidinium ethyl, 2'-carbamate, 2'-aminooxy, 2'-acetamido and locked nucleic acid. In a preferred embodiment, the sugar modification is 2'-O-methoxyethyl.

The provided antisense compounds can be 13 to 80 nucleobases in length, 13 to 50 nucleobases in length, 13 to 30 nucleobases in length, 20 to 30 nucleobases in length, 15 to 25 nucleobases in length or 20 nucleobases in length.

Chimeric antisense compounds useful for the modulation of splicing can have a variety of different chemical motifs (i.e. arrangement of 2'-deoxyribose and 2'-modified nucleosides). Representative examples of 20-nucleobase chimeric antisense compound motifs are shown in Table 1, wherein the number listed represents the number of nucleosides for each region. Bold numbers represent nucleosides with a RNA-like sugar moiety (a 2'-modified sugar) and numbers with regular type-face represent nucleosides with a DNA-like sugar moiety (2'-deoxyribose).

TABLE 1

Representative Motifs

4-3-1-3-1-3-5
5-3-1-3-1-3-4
3-2-2-3-2-3-5
5-3-2-3-2-2-3
3-3-2-3-2-3-4
2-3-1-3-1-3-1-3-3
4-3-1-2-2-3-5
4-3-2-3-2-3-3

In some embodiments, the cells or tissues are derived from adipose or liver. In other embodiments, the compounds are targeted to a splice site, including aberrant splice sites and cryptic splice sites.

Further provided are methods of enhancing cellular uptake, methods of enhancing pharmacologic activity and methods of modulating tissue distribution of an RNase H-independent antisense oligonucleotide with uniformly modified sugar residues by substituting selected modified sugar residues with 2'-deoxyribose sugar residues.

In one embodiment of the methods, the sugar modification is selected from 2'-O-methoxyethyl, 2'-fluoro, 2'-dimethylaminooxyethoxy, 2'-dimethylaminoethoxyethoxy, 2'-guanidinium, 2'-O-guanidinium ethyl, 2'-carbamate, 2'-aminooxy, 2'-acetamido and locked nucleic acid. In a preferred embodiment, the sugar modification is 2'-O-methoxyethyl.

In one embodiment, cellular uptake occurs in adipose tissue. In another embodiment, cellular uptake occurs in the liver.

In further embodiments, cellular uptake occurs in vitro, ex vivo or in vivo.

In one embodiment, modulation of tissue distribution results in an increase in oligonucleotide concentration in adipose tissue. In another embodiment, modulation of tissue distribution results in an increase in oligonucleotide concentration in liver tissue.

Also provided are chimeric RNase H-independent antisense compounds which exhibit enhanced cellular uptake relative to uniformly modified RNase H-independent compounds. Further provided are chimeric RNase H-independent antisense compounds which modulate splicing of a selected target mRNA. In one embodiment, the compound specifically hybridizes with a splice site of a selected target mRNA. In further embodiments, the splice site can be an aberrant splice site or a cryptic splice site.

Compounds

The term "oligomeric compound" refers to a polymeric structure capable of hybridizing to a region of a nucleic acid molecule. This term includes oligonucleotides, oligonucleosides, oligonucleotide analogs, oligonucleotide mimetics and chimeric combinations of these. Oligomeric compounds are routinely prepared linearly but can be joined or otherwise prepared to be circular. Moreover, branched structures are known in the art. An "antisense compound" or "antisense oligomeric compound" refers to an oligomeric compound that is at least partially complementary to the region of a nucleic acid molecule to which it hybridizes and which modulates (increases or decreases) its expression. Consequently, while all antisense compounds can be said to be oligomeric compounds, not all oligomeric compounds are antisense compounds. An "antisense oligonucleotide" is an antisense compound that is a nucleic acid-based oligomer. An antisense oligonucleotide can be chemically modified. Non-limiting examples of oligomeric compounds include primers, probes, antisense compounds, antisense oligonucleotides, external guide sequence (EGS) oligonucleotides and alternate splicers. In one embodiment, the oligomeric compound comprises an antisense strand hybridized to a sense strand. Oligomeric compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self complementarity to allow for hybridization and formation of a fully or partially double-stranded compound.

The oligomeric compounds provided herein comprise compounds from about 8 to about 80 nucleobases (i.e. from about 8 to about 80 linked nucleosides). One of ordinary skill in the art will appreciate that this comprehends antisense compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases.

In one embodiment, the antisense compounds comprise 13 to 80 nucleobases. One having ordinary skill in the art will appreciate that this embodies antisense compounds of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases.

In one embodiment, the antisense compounds comprise 13 to 50 nucleobases. One having ordinary skill in the art will appreciate that this embodies antisense compounds of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, or 50 nucleobases.

In one embodiment, the antisense compounds comprise 13 to 30 nucleobases. One having ordinary skill in the art will appreciate that this embodies antisense compounds of 13, 14, 15, 16, 17, 18, 19, 20, 21, 22, 23, 24, 25, 26, 27, 28, 29 or 30 nucleobases.

In one embodiment, the antisense compounds comprise 20 to 30 nucleobases. One having ordinary skill in the art will appreciate that this embodies antisense compounds of 20, 21, 22, 23, 24, 25, 26, 27, 28, 29, or 30 nucleobases.

In one embodiment, the antisense compounds comprise 15 to 25 nucleobases. One having ordinary skill in the art will appreciate that this embodies antisense compounds of 15, 16, 17, 18, 19, 20, 21, 22, 23, 24 or 25.

In one embodiment, the antisense compounds comprise 20 nucleobases.

In one embodiment, the antisense compounds comprise 19 nucleobases.

In one embodiment, the antisense compounds comprise 18 nucleobases.

In one embodiment, the antisense compounds comprise 17 nucleobases.

In one embodiment, the antisense compounds comprise 16 nucleobases.

In one embodiment, the antisense compounds comprise 15 nucleobases.

In one embodiment, the antisense compounds comprise 14 nucleobases.

In one embodiment, the antisense compounds comprise 13 nucleobases.

In one aspect, antisense compounds 8-80 nucleobases in length comprising a stretch of at least eight (8) consecutive nucleobases selected from within the illustrative antisense compounds are considered to be suitable antisense compounds.

In one embodiment, compounds include oligonucleotide sequences that comprise at least the 8 consecutive nucleobases from the 5'-terminus of one of the illustrative antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Other compounds are represented by oligonucleotide sequences that comprise at least the 8 consecutive nucleobases from the 3'-terminus of one of the illustrative antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). It is also understood that compounds may be represented by oligonucleotide sequences that comprise at least 8 consecutive nucleobases from an internal portion of the sequence of an illustrative compound, and may extend in either or both directions until the oligonucleotide contains about 8 to about 80 nucleobases.

One having skill in the art armed with the antisense compounds illustrated herein will be able, without undue experimentation, to identify further antisense compounds.

Hybridization

"Hybridization" means the pairing of complementary strands of oligomeric compounds. While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound is specifically hybridizable when there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

"Stringent hybridization conditions" or "stringent conditions" refer to conditions under which an oligomeric compound will hybridize to its target sequence, but to a minimal number of other sequences. Stringent conditions are sequence-dependent and will be different in different circumstances, and "stringent conditions" under which oligomeric compounds hybridize to a target sequence are determined by the nature and composition of the oligomeric compounds and the assays in which they are being investigated.

Complementarity

"Complementarity," as used herein, refers to the capacity for precise pairing between two nucleobases on either two oligomeric compound strands or an antisense compound with its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be a complementary position.

"Complementarity" can also be viewed in the context of an antisense compound and its target, rather than in a base by base manner. The antisense compound and the further DNA or RNA are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the antisense compound and a target nucleic acid. One skilled in the art recognizes that the inclusion of mismatches is possible without eliminating the activity of the antisense compound. Compounds provided herein are therefore directed to those antisense compounds that may contain up to about 20% nucleotides that disrupt base pairing of the antisense compound to the target. Preferably the compounds contain no more than about 15%, more preferably not more than about 10%, most preferably not more than 5% or no mismatches. The remaining nucleotides do not disrupt hybridization (e.g., universal bases).

It is understood in the art that incorporation of nucleotide affinity modifications may allow for a greater number of mismatches compared to an unmodified compound. Similarly, certain oligonucleotide sequences may be more tolerant to mismatches than other oligonucleotide sequences. One of the skill in the art is capable of determining an appropriate number of mismatches between oligonucleotides, or between an oligonucleotide and a target nucleic acid, such as by determining melting temperature.

Identity

Antisense compounds, or a portion thereof, may have a defined percent identity to a SEQ ID NO, or a compound having a specific Isis number. As used herein, a sequence is identical to the sequence disclosed herein if it has the same nucleobase pairing ability. For example, a RNA which contains uracil in place of thymidine in the disclosed sequences would be considered identical as they both pair with adenine. This identity may be over the entire length of the oligomeric compound, or in a portion of the antisense compound (e.g., nucleobases 1-20 of a 27-mer may be compared to a 20-mer to determine percent identity of the oligomeric compound to the SEQ ID NO.) It is understood by those skilled in the art that an antisense compound need not have an identical sequence to those described herein to function similarly to the antisense compound described herein. Shortened versions of antisense compound taught herein, or non-identical versions of the antisense compound taught herein are also contemplated. Non-identical versions are those wherein each base does not have the same pairing activity as the antisense compounds disclosed herein. Bases do not have the same pairing activity by being shorter or having at least one abasic site. Alternatively, a non-identical version can include at least one base replaced with a different base with different pairing activity (e.g., G can be replaced by C, A, or T). Percent identity is calculated according to the number of bases that have identical base pairing corresponding to the SEQ ID NO or antisense compound to which it is being compared. The non-identical bases may be adjacent to each other, dispersed through out the oligonucleotide, or both.

For example, a 16-mer having the same sequence as nucleobases 2-17 of a 20-mer is 80% identical to the 20-mer. Alternatively, a 20-mer containing four nucleobases not identical to the 20-mer is also 80% identical to the 20-mer. A 14-mer having the same sequence as nucleobases 1-14 of an 18-mer is 78% identical to the 18-mer. Such calculations are well within the ability of those skilled in the art.

The percent identity is based on the percent of nucleobases in the original sequence present in a portion of the modified sequence. Therefore, a 30 nucleobase antisense compound comprising the full sequence of the complement of a 20 nucleobase active target segment would have a portion of 100% identity with the complement of the 20 nucleobase active target segment, while further comprising an additional 10 nucleobase portion. The complement of an active target segment may constitute a single portion. In a preferred embodiment, the oligonucleotides are at least about 80%, more preferably at least about 85%, even more preferably at least about 90%, most preferably at least 95% identical to at least a portion of the complement of the active target segments presented herein.

It is well known by those skilled in the art that it is possible to increase or decrease the length of an antisense compound and/or introduce mismatch bases without eliminating activity. For example, in Woolf et al. (Proc. Natl. Acad. Sci. USA 89:7305-7309, 1992, incorporated herein by reference), a series of ASOs 13-25 nucleobases in length were tested for their ability to induce cleavage of a target RNA. ASOs 25 nucleobases in length with 8 or 11 mismatch bases near the ends of the ASOs were able to direct specific cleavage of the target mRNA, albeit to a lesser extent than the ASOs that contained no mismatches. Similarly, target specific cleavage was achieved using a 13 nucleobase ASOs, including those with 1 or 3 mismatches. Maher and Dolnick (Nuc. Acid. Res. 16:3341-3358,1988, incorporated herein by reference) tested a series of tandem 14 nucleobase ASOs, and a 28 and 42 nucleobase ASOs comprised of the sequence of two or three of the tandem ASOs, respectively, for their ability to arrest translation of human DHFR in a rabbit reticulocyte assay. Each of the three 14 nucleobase ASOs alone were able to inhibit translation, albeit at a more modest level than the 28 or 42 nucleobase ASOs. It is understood that antisense compounds can vary in length and percent complementarity to the target provided that they maintain the desired activity. Methods to determine desired activity are disclosed herein and well known to those skilled in the art.

Chemical Modifications

As is known in the art, a nucleoside is a base-sugar combination. The base portion of the nucleoside is normally a heterocyclic base (sometimes referred to as a "nucleobase" or simply a "base"). The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. Within oligonucleotides, the phosphate groups are commonly referred to as forming the internucleoside backbone of the oligonucleotide. The normal linkage or backbone of RNA and DNA is a 3' to 5' phosphodiester linkage. It is often preferable to include chemical modifications in oligonucleotides to alter their activity. Chemical modifications can alter oligonucleotide activity by, for example: increasing affinity of an antisense oligonucleotide for its target RNA, increasing nuclease resistance, and/or altering the pharmacokinetics of the oligonucleotide. The use of chemistries that increase the affinity of an oligonucleotide for its target can allow for the use of shorter oligonucleotide compounds.

The term "nucleobase" or "heterocyclic base moiety" as used herein, refers to the heterocyclic base portion of a nucleoside. In general, a nucleobase is any group that contains one or more atom or groups of atoms capable of hydrogen bonding to a base of another nucleic acid. In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable to the compounds described herein. The terms modified nucleobase and nucleobase mimetic can overlap but generally a modified nucleobase refers to a nucleobase that is fairly similar in structure to the parent nucleobase, such as for example a 7-deaza purine, a 5-methyl cytosine, or a G-clamp, whereas a nucleobase mimetic would include more complicated structures, such as for example a tricyclic phenoxazine nucleobase mimetic. Methods for preparation of the above noted modified nucleobases are well known to those skilled in the art.

Antisense compounds provided herein may also contain one or more nucleosides having modified sugar moieties. The furanosyl sugar ring of a nucleoside can be modified in a number of ways including, but not limited to, addition of a substituent group, bridging of two non-geminal ring atoms to form a bicyclic nucleic acid (BNA) and substitution of an atom or group such as —S—, —N(R)— or —C($R_1$)($R_2$) for the ring oxygen at the 4'-position. Modified sugar moieties are well known and can be used to alter, typically increase, the affinity of the antisense compound for its target and/or increase nuclease resistance. A representative list of preferred modified sugars includes but is not limited to bicyclic modified sugars (BNA's), including LNA and ENA (4'-(CH$_2$)$_2$—O-2' bridge); and substituted sugars, especially 2'-substituted sugars having a 2'-F, 2'-OCH$_2$ or a 2'-O(CH$_2$)$_2$—OCH$_3$ substituent group. Sugars can also be replaced with sugar mimetic groups among others. Methods for the preparations of modified sugars are well known to those skilled in the art.

The compounds described herein may include internucleoside linking groups that link the nucleosides or otherwise modified monomer units together thereby forming an antisense compound. The two main classes of internucleoside linking groups are defined by the presence or absence of a phosphorus atom. Representative phosphorus containing internucleoside linkages include, but are not limited to, phosphodiesters, phosphotriesters, methylphosphonates, phosphoramidate, and phosphorothioates. Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)2-O—); and N,N'-dimethylhydrazine (—CH$_2$—N(CH$_3$)—N(CH$_3$)—). Antisense compounds having non-phosphorus internucleoside linking groups are referred to as oligonucleosides. Modified internucleoside linkages, compared to natural phosphodiester linkages, can be used to alter, typically increase, nuclease resistance of the antisense compound. Internucleoside linkages having a chiral atom can be prepared racemic, chiral, or as a mixture. Representative chiral internucleoside linkages include, but are not limited to, alkylphosphonates and phosphorothioates. Methods of preparation of phosphorous-containing and non-phosphorous-containing linkages are well known to those skilled in the art.

As used herein the term "mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target. Representative examples of a sugar mimetic include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al., Nuc Acid Res. 2000, 28:2911-14, incorporated herein by reference). Methods of synthesis of sugar, nucleoside and nucleobase mimetics are well known to those skilled in the art.

As used herein the term "nucleoside" includes, nucleosides, abasic nucleosides, modified nucleosides, and nucleosides having mimetic bases and/or sugar groups.

As used herein, the term "oligonucleotide" refers to an oligomeric compound which is an oligomer or polymer of ribonucleic acid (RNA) or deoxyribonucleic acid (DNA). This term includes oligonucleotides composed of naturally- and non-naturally-occurring nucleobases, sugars and covalent internucleoside linkages, possibly further including non-nucleic acid conjugates.

The present disclosure provides compounds having reactive phosphorus groups useful for forming internucleoside linkages including for example phosphodiester and phosphorothioate internucleoside linkages. Methods of preparation and/or purification of precursors or antisense compounds are not a limitation of the compositions or methods provided herein. Methods for synthesis and purification of DNA, RNA, and the antisense compounds provided herein are well known to those skilled in the art.

As used herein the term "chimeric antisense compound" refers to an antisense compound, having at least one sugar, nucleobase and/or internucleoside linkage that is differentially modified as compared to the other sugars, nucleobases and internucleoside linkages within the same oligomeric compound. The remainder of the sugars, nucleobases and internucleoside linkages can be independently modified or unmodified. In general a chimeric oligomeric compound will have modified nucleosides that can be in isolated positions or grouped together in regions that will define a particular motif Any combination of modifications and or mimetic groups can comprise a chimeric oligomeric compound.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease that cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

As used herein, the term "fully modified motif" refers to an antisense compound comprising a contiguous sequence of nucleosides wherein essentially each nucleoside is a sugar modified nucleoside having uniform modification.

The compounds described herein contain one or more asymmetric centers and thus give rise to enantiomers, diastereomers, and other stereoisomeric configurations that may be defined, in terms of absolute stereochemistry, as (R) or (S), α or β, or as (D) or (L) such as for amino acids et al. The present disclosure is meant to include all such possible isomers, as well as their racemic and optically pure forms.

In one aspect, antisense compounds are modified by covalent attachment of one or more conjugate groups. Conjugate groups may be attached by reversible or irreversible attachments. Conjugate groups may be attached directly to antisense compounds or by use of a linker. Linkers may be mono- or bifunctional linkers. Such attachment methods and linkers are well known to those skilled in the art. In general, conjugate groups are attached to antisense compounds to modify one or more properties. Such considerations are well known to those skilled in the art.

Oligomer Synthesis

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Antisense compounds can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The disclosure is not limited by the method of antisense compound synthesis.

Oligomer Purification and Analysis

Methods of oligonucleotide purification and analysis are known to those skilled in the art. Analysis methods include capillary electrophoresis (CE) and electrospray-mass spectroscopy. Such synthesis and analysis methods can be performed in multi-well plates. The methods described herein are not limited by the method of oligomer purification.

Assaying Modulation of Splicing

Modulation of splicing can be assayed in a variety of ways known in the art. Target mRNA levels can be quantitated by, e.g., Northern blot analysis, competitive polymerase chain reaction (PCR), or real-time PCR. RNA analysis can be performed on total cellular RNA or poly(A)+mRNA by methods known in the art. Methods of RNA isolation are taught in, for example, Ausubel, F. M. et al., *Current Protocols in Molecular Biology*, Volume 1, pp. 4.1.1-4.2.9 and 4.5.1-4.5.3, John Wiley & Sons, Inc., 1993.

Northern blot analysis is routine in the art and is taught in, for example, Ausubel, F. M. et al., *Current Protocols in Molecular Biology*, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Levels of a protein encoded by a target mRNA can be quantitated in a variety of ways well known in the art, such as immunoprecipitation, Western blot analysis (immunoblotting), ELISA or fluorescence-activated cell sorting (FACS). Antibodies directed to a protein encoded by a target mRNA can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., 1991.

Kits, Research Reagents, Diagnostics, and Therapeutics

The oligomeric compounds provided herein can be utilized for diagnostics, therapeutics, prophylaxis and as research reagents and kits. Furthermore, antisense compounds, which are able to inhibit gene expression or modulate splicing with specificity, are often used by those of ordinary skill to elucidate the function of particular genes or gene products or to distinguish between functions of various members of a biological pathway.

For use in kits and diagnostics, the oligomeric compounds described herein, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more compounds or compositions provided herein are compared to control cells or tissues not treated with compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today,* 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.,* 2000, 97, 1976-81), protein arrays and proteomics (Celis, et al., *FEBS Lett.*, 2000, 480, 2-16; Jungblut, et al., *Electrophoresis,* 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry,* 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer,* 1999, 35, 1895-904) and mass spectrometry methods (To, *Comb. Chem. High Throughput Screen,* 2000, 3, 235-41).

Compounds described herein can be used to modulate splicing of a target mRNA in an animal, such as a human. In one non-limiting embodiment, the methods comprise the step of administering to said animal an effective amount of an antisense compound that modulates splicing of a target mRNA.

For example, modulation of splicing of a target mRNA can be measured by determining levels of mRNA splicing products in a bodily fluid, tissue or organ of the animal. Bodily fluids include, but are not limited to, blood (serum or plasma), lymphatic fluid, cerebrospinal fluid, semen, urine, synovial fluid and saliva and can be obtained by methods routine to those skilled in the art. Tissues or organs include, but are not limited to, blood (e.g., hematopoietic cells, such as human hematopoietic progenitor cells, human hematopoietic stem cells, CD34+ cells CD4+ cells), lymphocytes and other blood lineage cells, skin, bone marrow, spleen, thymus, lymph node, brain, spinal cord, heart, skeletal muscle, liver, pancreas, prostate, kidney, lung, oral mucosa, esophagus, stomach, ilium, small intestine, colon, bladder, cervix, ovary, testis, mammary gland, adrenal gland, and adipose (white and brown). Samples of tissues or organs can be routinely obtained by biopsy. In some alternative situations, samples of tissues or organs can be recovered from an animal after death.

The effects of treatment with the oligomeric compounds can be assessed by measuring biomarkers associated with modulation of splicing of a target mRNA in the aforementioned fluids, tissues or organs, collected from an animal contacted with one or more compounds, by routine clinical methods known in the art. These biomarkers include but are not limited to: glucose, cholesterol, lipoproteins, triglycerides, free fatty acids and other markers of glucose and lipid metabolism; liver transaminases, bilirubin, albumin, blood urea nitrogen, creatine and other markers of kidney and liver function; interleukins, tumor necrosis factors, intracellular adhesion molecules, C-reactive protein and other markers of inflammation; testosterone, estrogen and other hormones; tumor markers; vitamins, minerals and electrolytes.

The compounds disclosed herein can be utilized in pharmaceutical compositions by adding an effective amount of a compound to a suitable pharmaceutically acceptable diluent or carrier. The compounds can also be used in the manufacture of a medicament for the treatment of diseases and disorders related to alterations in splicing.

Methods whereby bodily fluids, organs or tissues are contacted with an effective amount of one or more of the antisense compounds or compositions of the disclosure are also contemplated. Bodily fluids, organs or tissues can be contacted with one or more of the compounds of the disclosure resulting in modulation of splicing of target mRNA in the cells of bodily fluids, organs or tissues. An effective amount can be determined by monitoring the modulatory effect of the antisense compound or compounds or compositions on target nucleic acids or their products by methods routine to the skilled artisan. Further contemplated are ex vivo methods of treatment whereby cells or tissues are isolated from a subject, contacted with an effective amount of the antisense compound or compounds or compositions and reintroduced into the subject by routine methods known to those skilled in the art.

Salts, Prodrugs and Bioequivalents

The antisense compounds described herein comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs and pharmaceutically acceptable salts of the antisense compounds, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes, chemicals, and/or conditions. In particular, prodrug versions of the oligonucleotides are prepared as SATE ((S-acetyl-2-thioethyl) phosphate) derivatives according to the methods disclosed in WO 93/24510 or WO 94/26764. Prodrugs can also include antisense compounds wherein one or both ends comprise nucleobases that are cleaved (e.g., by incorporating phosphodiester backbone linkages at the ends) to produce the active compound.

The term "pharmaceutically acceptable salts" refers to physiologically and pharmaceutically acceptable salts of the compounds: i.e., salts that retain the desired biological activity of the parent compound and do not impart undesired toxicological effects thereto. Sodium salts of antisense oligonucleotides are useful and are well accepted for therapeutic administration to humans. In another embodiment, sodium salts of dsRNA compounds are also provided.

Formulations

The antisense compounds described herein may also be admixed, encapsulated, conjugated or otherwise associated with other molecules, molecule structures or mixtures of compounds.

The present disclosure also includes pharmaceutical compositions and formulations which include the antisense compounds described herein. The pharmaceutical compositions may be administered in a number of ways depending upon whether local or systemic treatment is desired and upon the area to be treated. In a preferred embodiment, administration is topical to the surface of the respiratory tract, particularly pulmonary, e.g., by nebulization, inhalation, or insufflation of powders or aerosols, by mouth and/or nose.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers, finely divided solid carriers, or both, and then, if necessary, shaping the product (e.g., into a specific particle size for delivery). In a preferred embodiment, the pharmaceutical formulations are prepared for pulmonary administration in an appropriate solvent, e.g., water or normal saline, possibly in a sterile formulation, with carriers or other agents to allow for the formation of droplets of the desired diameter for delivery using inhalers, nasal delivery devices, nebulizers, and other devices for pulmonary delivery. Alternatively, the pharmaceutical formulations may be formulated as dry powders for use in dry powder inhalers.

A "pharmaceutical carrier" or "excipient" can be a pharmaceutically acceptable solvent, suspending agent or any other pharmacologically inert vehicle for delivering one or more nucleic acids to an animal and are known in the art. The excipient may be liquid or solid and is selected, with the planned manner of administration in mind, so as to provide for the desired bulk, consistency, etc., when combined with a nucleic acid and the other components of a given pharmaceutical composition.

Combinations

Compositions provided herein can contain two or more antisense compounds. In another related embodiment, compositions can contain one or more antisense compounds, particularly oligonucleotides, targeted to a first nucleic acid and one or more additional antisense compounds targeted to a second nucleic acid target. Alternatively, compositions provided herein can contain two or more antisense compounds targeted to different regions of the same nucleic acid target. Two or more combined compounds may be used together or sequentially. Compositions can also be combined with other non-antisense compound therapeutic agents.

Nonlimiting Disclosure and Incorporation by Reference

While certain compounds, compositions and methods provided herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

EXAMPLE 1

EGFP-654 Transgenic Mouse Model

EGFP-654 transgenic mice transcribe the EGFP-654 transgene throughout the body. In this mouse model, the transgene encoding enhanced green fluorescent protein (EGFP) is interrupted by an aberrantly spliced mutated intron 2 of the human β-globin gene. The mutation at nucleotide 654 of intron 2 of human β-globin activates aberrant splice sites and leads to retention of the intron fragment in spliced mRNA, preventing proper translation of EGFP. Aberrant splicing of this intron prevents expression of EGFP-654 in all tissues. Blocking the aberrant splice site restores normal pre-mRNA splicing and EGFP expression. Thus, EGFP-654 transgenic mice can be used to evaluate oligomeric compounds designed to modulate splicing. Generation of EGFP-654 transgenic mice and control EGFP-WT mice is described in Sazani et al. (2002, *Nature Biotechnol.* 20:1228-1233). Briefly, plasmid CX-EGFP-654 was constructed from plasmid CXEGFP (Okabe et al. 1997, *FEBS Lett.* 407:313-319) as described by Sazani et al. (2001, *Nucleic Acids Res.* 29:3965-3974). To generate the CX-EGFP-WT plasmid, an EcoNI-PpumI fragment of β-globin intron 2 from the CX-EGFG-654 plasmid was replaced by the same fragment from the intron 2 of the wild-type β-globin gene. Transgenic mice were produced using standard procedures by microinjection of the 3.8 kb PstI/SalI fragments of CX-EGFP-654 and CX-EGFP-WT into fertilized FVB/N mouse embryos.

EXAMPLE 2

Design of Oligomeric Compounds for Modulation of Splicing

In accordance with the present disclosure, a series of oligomeric compounds was designed to modulate splicing of selected pre-mRNAs. The sequence and motif of each compound is shown in Table 2. Compounds were designed to target either the 5' splice site of intron 1 of Bcl-x, or nucleotide 623 (β-globin 623) or 654 (β-globin 654) of the human β-globin intron 2 sequence of the EGFP-654 transgene. Bold residues represent 2'-O-methoxyethyl nucleotides and regular type-face nucleotides represent 2'-deoxyribonucleotides. The "motif" indicates the number of 2'-O-methoxyethyl and 2'-deoxyribonucleotides in each region. Uniformly modified compounds comprise 2'-O-methoxyethyl, also known as 2'-MOE, nucleotides at each position.

TABLE 2

Oligomeric Compounds for Modulation of Splicing

| mRNA Target | ISIS No. | Sequence | SEQ ID NO | Motif |
|---|---|---|---|---|
| Bcl-x | 105751 | TGGTTCTTACCCAGCCGCCG | 1 | Uniformly Modified |
| Bcl-x | 355087 | TGGTTCTTACCCAGCCGCCG | 1 | 4-3-1-2-2-3-5 |
| Bcl-x | 355088 | TGGTTCTTACCCAGCCGCCG | 1 | 4-3-1-3-1-3-5 |
| Bcl-x | 355089 | TGGTTCTTACCCAGCCGCCG | 1 | 3-2-2-3-2-3-5 |
| Bcl-x | 355090 | TGGTTCTTACCCAGCCGCCG | 1 | 1-1-1-1-1-1-1-1-1-1-1-1-1-1-1-1-1-1-1-1 |
| Bcl-x | 355091 | TGGTTCTTACCCAGCCGCCG | 1 | 2-2-2-2-2-2-2-2-2-2 |
| β-globin 623 | 379227 | GTTATTCTTTAGAATGGTGC | 2 | Uniformly Modified |
| β-globin 623 | 379326 | GTTATTCTTTAGAATGGTGC | 2 | 4-3-1-3-1-3-5 |
| β-globin 623 | 379327 | GTTATTCTTTAGAATGGTGC | 2 | 5-3-1-3-1-3-4 |
| β-globin 623 | 379328 | GTTATTCTTTAGAATGGTGC | 2 | 3-2-2-3-2-3-5 |
| β-globin 623 | 379329 | GTTATTCTTTAGAATGGTGC | 2 | 5-3-2-3-2-2-3 |
| β-globin 623 | 379330 | GTTATTCTTTAGAATGGTGC | 2 | 3-3-2-3-2-3-4 |
| β-globin 623 | 379331 | GTTATTCTTTAGAATGGTGC | 2 | 2-3-1-3-1-3-1-3-3 |
| β-globin 654 | 379234 | TGCTATTACCTTAACCCAGA | 3 | Uniformly Modified |
| β-globin 654 | 379332 | TGCTATTACCTTAACCCAGA | 3 | 4-3-1-3-1-3-5 |
| β-globin 654 | 379333 | TGCTATTACCTTAACCCAGA | 3 | 5-3-1-3-1-3-4 |
| β-globin 654 | 379334 | TGCTATTACCTTAACCCAGA | 3 | 3-2-2-3-2-3-5 |
| β-globin 654 | 379335 | TGCTATTACCTTAACCCAGA | 3 | 4-3-2-3-2-3-3 |
| β-globin 654 | 379336 | TGCTATTACCTTAACCCAGA | 3 | 3-3-2-3-2-3-4 |
| β-globin 654 | 379337 | TGCTATTACCTTAACCCAGA | 3 | 2-3-1-3-1-3-1-3-3 |

EXAMPLE 3

Modulation of Bcl-x Splicing by Chimeric Oligomeric Compounds in Vitro

The human prostatic carcinoma cell line PC-3 was obtained from the American Type Culture Collection (ATCC) (Manassas, Va.). PC-3 cells were routinely cultured in Ham's F12K medium with 2 mM L-glutamine adjusted to contain 1.5 g/L sodium bicarbonate supplemented with 10% fetal bovine serum (Invitrogen Life Technologies, Carlsbad, Calif.) and antibiotics (Invitrogen Life Technologies, Carlsbad, Calif.). Cells were routinely passaged by trypsinization and dilution when they reached approximately 90% confluence.

In accordance with the present disclosure, uniformly 2'-MOE-modified and chimeric antisense compounds were screened in PC-3 cells for modulation of Bcl-x splicing. Human Bcl-x has a long form, Bcl-$x_L$ and a short form, Bcl-$x_S$, which results from alternative splicing. The two isoforms are identical except that Bcl-$x_S$ lacks the 3'-most 327 nucleotides of exon 1, resulting in a protein that is 63 amino acids shorter than Bcl-$x_L$. The short isoform is generated when splicing occurs using a cryptic 5'splice site at nucleotide position 509, rather than the 5' splice site at nucleotide 698. The functions of the two isoforms differ, with Bcl-$x_L$ being anti-apoptotic while Bcl-$x_S$ promotes apoptosis. The Bcl-x antisense compounds provided herein were designed to target the 5' splice site between exon 1 and intron 1 of the Bcl-x pre-mRNA, such that splicing is redirected to increase the ratio of short form to long form.

PC-3 cells were transfected with 1, 10 or 100 nM of either ISIS 105751, ISIS 355087, ISIS 355088, ISIS 355089, ISIS 355090 or ISIS 355091 using Lipofectamine 2000. After 24 h, total RNA was isolated using TRI-reagent according to the supplier's instructions and RT-PCR reactions using $^{32}$P-ATP were performed using primers that flank the alternatively spliced intron 1. To determine the levels of Bcl-$x_L$ and Bcl-$x_S$, PCR products were separated by electrophoresis on 10% polyacrylamide gels and the gels were subjected to autoradiography. In untransfected cells, little to none of the short isoforms of Bcl-x was detected. In contrast, when PC-3 cells were transfected with either the fully modified antisense compound ISIS 105751, or any of the chimeric antisense compounds, levels of Bcl-$x_S$ increased in a dose-dependent manner while levels of Bcl-$x_L$ decreased. Thus, the chimeric antisense oligomeric compounds provided herein effectively modulate splicing of a target pre-mRNA in vitro.

EXAMPLE 4

Modulation of Bcl-x Splicing in EGFP-654 Mice

Bcl-x chimeric oligomeric compounds were next evaluated in EGFP-654 mice to assess their ability to modulate splicing in vivo. EGFP-654 transgenic mice were treated with 25 mg/kg of ISIS 105751, ISIS 355088, ISIS 355089 or ISIS 355090 for seven or fourteen days. All oligonucleotides were dissolved in 0.9% saline at 2.5 mg/ml and 200 µL of oligonucleotide solution was used per injection. Intraperitoneal injections were given daily, at approximately the same time each day. Mice were sacrificed 24 hours following the last injection and liver and adipose tissues were collected.

Tissues were homogenized in 800 µL of TRI-Reagent and samples were centrifuged for 1 min to remove cellular debris. The supernatant was transferred to a new tube and total RNA was isolated following the TRI-Reagent supplier's protocol. To test for a shift in the splicing pattern of Bcl-x pre-mRNA, the RNA was analyzed by RT-PCR using primers that flank the alternatively spliced intron. $^{32}$P-ATP was included in the PCR reaction mixture. The PCR products were separated by electrophoresis on a 10% polyacrylamide gel and the gels were subjected to autoradiography.

In the seven day treatment group, mice treated with Bcl-x chimeric antisense compounds ISIS 355088 and ISIS 355089 showed low levels of the short isoform of Bcl-x in the liver, while little to none was observed in mice treated with ISIS 150751 or ISIS 355090. In adipose tissue, treatment with ISIS 355089 resulted in a significant increase in the ratio of short form to long form, while low levels of Bcl-$x_S$ were detected in adipose tissues from mice treated with the remaining compounds.

In the fourteen day treatment group, liver samples from mice treated with each of the chimeric antisense compounds revealed low levels of Bcl-$x_S$, but little to none was observed in mice treated with the uniformly 2'MOE modified compound ISIS 150751. In adipose tissue, the short isoform of Bcl-x was detected regardless of the antisense compound tested; however, treatment with ISIS 355089 showed the greatest activity, resulting in a significant increase in the ratio of short form to long form.

To further evaluate ISIS 355089, two EGFP-654 mice were treated with 25 mg/kg by daily intraperitoneal injection for three days. As described above, mice were sacrificed 24 hours after the final injection and liver and adipose tissue were collected for RT-PCR analysis of Bcl-x mRNA. As expected, treatment with ISIS 355089 resulted in an increase in Bcl-$x_S$ in both liver and adipose. In addition, when comparing liver tissue to adipose tissue, the ratio of Bcl-$x_S$ to Bcl-$x_L$ is greater in adipose tissue than in liver.

Together these results demonstrate that the chimeric antisense oligomeric compounds provided herein effectively modulate splicing of a target pre-mRNA in vivo. Furthermore, modulation of splicing is particularly effective in adipose tissue.

EXAMPLE 5

Modulation of EGFP-654 pre-mRNA Splicing in Vivo

The EGFP-654 transgenic mouse system was used to further evaluate chimeric oligomeric compounds for modulation of splicing. As described in Example 1, the EGFP-654 transgene contains the EGFP coding sequence interrupted by a mutated intron 2 of the human β-globin gene which contains an aberrant splice site. Due to aberrant splicing, EGFP is not expressed. Blockade of the aberrant splice site would allow EGFP expression in all tissues. Chimeric antisense compounds were designed to prevent aberrant splicing and restore correct pre-mRNA splicing of the transgene. β-globin 623 and β-globin 654 target nucleotide 623 and 654, respectively, of the intron.

EGFP-654 transgenic mice were treated for three days by intraperitoneal injection of β-globin 623 compounds ISIS 379328 (chimeric) or ISIS 379227 (uniformly modified), or β-globin 654 compounds ISIS 379234 (uniformly modified) or ISIS 379334 (chimeric), at a dose of 20 mg/kg. Mice treated with Bcl-x compounds ISIS 150751 and ISIS 355089 were included as negative controls for EGFP expression, as were saline-treated mice. EGFP-WT mice were included as positive controls for EGFP expression. All antisense oligonucleotides were dissolved in 0.9% saline at 2.5 mg/ml. 200 µL of oligonucleotide solution was used per injection. Injections were given daily, at approximately the same time each day. The mice were sacrificed 24 hours following the last injection and liver and adipose tissues were collected.

Tissues were homogenized in 800 μL of TRI-Reagent and samples were centrifuged for 1 min to remove cellular debris. The supernatant was transferred to a new tube and total RNA was isolated following the TRI-Reagent supplier's protocol. To test for a shift in the splicing pattern of EGFP-654 pre-mRNA, the RNA was analyzed by RT-PCR using primers that flank the alternatively spliced intron. $^{32}$P-ATP was included in the PCR reaction mixture. The PCR products were separated by electrophoresis on a 10% polyacrylamide gel and the gels were subjected to autoradiography. A correctly spliced EGFP-654 mRNA is smaller than the aberrantly spliced transcript and thus migrates faster in an electrophoretic gel.

In adipose tissue, mice treated with either of the β-globin 623 antisense compounds showed increased levels of correctly spliced EGFP relative to negative controls. The ratio of the correctly spliced to the aberrantly spliced was also increased. Minor amounts of correctly spliced EGFP were detected in mice treated with the β-globin 654 compounds. In liver tissue, background levels of correctly spliced EGFP were observed in negative control animals; however, treatment with either of the β-globin 623 antisense compounds resulted in an increase in levels of correctly spliced EGFP and an increase in the ratio of the correctly spliced form to the aberrantly spliced form. Although treatment with both chimeric and uniformly modified compounds resulted in an increase in correctly spliced EGFP relative to negative controls, the chimeric compounds were slightly more efficient at modulating splicing.

To further evaluate chimeric oligomeric compounds targeting β-globin 623, a second study was performed in EGFP-654 mice using a greater number of compounds. Using the procedures described above, EGFP-654 transgenic mice were treated with 20 mg/kg of ISIS 379227, ISIS 379326, ISIS 379327, ISIS 379328, ISIS 379329, ISIS 379330 or ISIS 379331 for three days. Saline-treated and EGFP-WT mice were included as negative and positive controls, respectively. Adipose and liver tissues were collected and RNA was isolated and subjected to RT-PCR and electrophoresis as described above.

In adipose tissue, treatment with any of the β-globin 623 compounds resulted in an increase in correctly spliced EGFP. The most efficient compounds were chimeric compounds ISIS 379328 and ISIS 379326. In liver tissue, each of the chimeric compounds significantly increased levels of correctly spliced EGFP; however, treatment with uniformly modified ISIS 379227 did not result in an increase in correctly spliced EGFP compared to saline control.

Taken together, these results further demonstrate that the chimeric antisense oligomeric compounds provided herein effectively modulate splicing of a target pre-mRNA in vivo and do so more efficiently than uniformly modified antisense compounds.

EXAMPLE 6

Concentration of Chimeric Oligomeric Compounds in Liver and Adipose Tissue

The chimeric oligomeric compounds provided herein have demonstrated greater pharmacologic activity (as measured by modulation of splicing activity) than counterpart uniformly modified compounds. One potential explanation for increased activity is enhanced cellular uptake of chimeric compounds. To assess oligonucleotide concentration in liver and adipose tissue of oligonucleotide-treated animals, EGFP-654 mice were treated with the uniformly modified and chimeric compounds shown in Table 3. Mice received three daily oligonucleotide doses of 20 mg/kg by intraperitoneal injection and were sacrificed one day following the last injection. Oligonucleotides were extracted from liver and adipose tissues and quantitated according to methods well known to one of ordinary skill in the art, such as, for example, the methods described in Geary et al. (1999, Anal. Biochem. 274:241-248). Table 3 shows the concentration of each oligonucleotide in liver and adipose tissue (in μg/g) and the percent concentration of chimeric oligonucleotides relative to their uniformly modified (UM) counterparts. "N.D." indicates not determined.

TABLE 3

Oligonucleotide concentration in liver and adipose tissue

| mRNA Target | ISIS No. | Motif | Adipose (μg/g) | Percent of UM | Liver (μg/g) | Percent of UM |
|---|---|---|---|---|---|---|
| Bcl-x | 105751 | Uniformly Modified | 10.13 | — | N.D. | — |
| Bcl-x | 355089 | 3-2-2-3-2-3-5 | 18.4 | 182 | N.D. | — |
| β-globin 623 | 379227 | Uniformly Modified | 20.44 | — | 1235.5 | — |
| β-globin 623 | 379326 | 4-3-1-3-1-3-5 | 9.26 | 45 | 141.02 | 114 |
| β-globin 623 | 379327 | 5-3-1-3-1-3-4 | 11.64 | 57 | 125.99 | 102 |
| β-globin 623 | 379328 | 3-2-2-3-2-3-5 | 31.5 | 154 | 179.53 | 145 |
| β-globin 623 | 379329 | 5-3-2-3-2-2-3 | 7.09 | 35 | 121.19 | 98 |
| β-globin 623 | 379330 | 3-3-2-3-2-3-4 | 12.0 | 59 | 135.3 | 110 |
| β-globin 623 | 379331 | 2-3-1-3-1-3-1-3-3 | 9.83 | 48 | 129.56 | 105 |
| β-globin 654 | 379234 | Uniformly Modified | 8.46 | — | 55.28 | — |
| β-globin 654 | 379332 | 4-3-1-3-1-3-5 | 11.95 | 141 | 123.75 | 224 |
| β-globin 654 | 379333 | 5-3-1-3-1-3-4 | 13.75 | 163 | 157.48 | 285 |
| β-globin 654 | 379334 | 3-2-2-3-2-3-5 | 14.92 | 176 | 101.25 | 183 |
| β-globin 654 | 379335 | 4-3-2-3-2-3-3 | 12.2 | 144 | 134.86 | 244 |
| β-globin 654 | 379336 | 3-3-2-3-2-3-4 | 6.0 | 71 | 123.07 | 223 |
| β-globin 654 | 379337 | 2-3-1-3-1-3-1-3-3 | 29.73 | 351 | 135.13 | 244 |

With the exception of several of the β-globin 623 compounds in adipose, the majority of chimeric antisense compounds showed significantly greater concentrations in both adipose and liver relative to their uniformly modified counterparts. These results suggest that chimeric compounds exhibit enhanced cellular uptake relative to uniformly modified compounds of the same sequence.

EXAMPLE 7

Modulation of Apoptosis by Bcl-x Chimeric Oligomeric Compounds

To determine whether an increase in the short isoform of Bcl-x results in increased levels of apoptosis in vivo, EGFP-654 mice were treated with a chimeric Bcl-x antisense compound and evaluated for apoptosis in adipose tissue. EGFP-654 mice were maintained on a high-fat diet for four weeks and subsequently treated with ISIS 355089 for 5 weeks. Saline treated animals served as controls. Mice were maintained on a high-fat diet throughout the treatment period. After treatment, the mice were weighed, sacrificed and the epididymal fat pads were isolated. The fat pads were weighed in order to determine whether treatment with ISIS 355089, and the subsequent accumulation of the short isoform of Bcl-x, would reduce the size of the adipose tissue. Table 4 shows the absolute weight in grams of the left (L) and right (R) fat pads and the percent of fat pad weight to total body weight.

TABLE 4

Weight of adipose tissue following treatment with ISIS 355089

| Measurement | Saline | ISIS 355089 |
|---|---|---|
| Fat pad weight (L) | 0.90 | 0.64 |
| Fat pad weight (R) | 0.87 | 0.75 |
| % of body weight (L) | 2.4 | 1.7 |
| % of body weight (R) | 2.4 | 2.0 |

As shown in Table 4, both overall weight of adipose tissue as well as the percent of adipose tissue to body weight was reduced following treatment with a chimeric oligomeric compound which increases the levels of Bcl-$x_S$.

Small sections of the adipose tissue were fixed and processed to determine whether the decrease in adipose tissue following treatment with ISIS 355089 resulted from an increase in apoptosis. Tissues were fixed in 10% formalin and embedded in paraffin. Samples were deparaffinized and antigen retrieval was performed using Citra solution. Slides were steamed in Citra solution for 30 min and then cooled for 20 min. Several blocking steps were performed before the primary antibody was added. Slides were incubated with primary antibody, rabbit anti-Caspase 3 in CAD with 10% goat serum, for 30 min at 37° C. The samples were rinsed with buffer 4 times prior to addition of biotinylated secondary antibody, goat anti-rabbit IgG in PBS with 0.1% Tween 20. After rinsing with buffer, the staining was developed using Vector ABC Elite Kit with HistoMark Black and Methyl Green. Slides positive for caspase 3 were indicated by blue staining The results demonstrated that adipose tissue from animals treated with ISIS 355089 had a greater number of apoptotic cells as compared to saline treated animals, suggesting that the decrease in adipose tissue weight resulted from an increase in cell death.

It is shown herein that chimeric antisense compounds function effectively as modulators of splicing, are taken up into cells and tissues efficiently and are capable of eliciting significant biological outcomes.

What is claimed is:

1. A chimeric RNase H-independent antisense compound 13 to 80 nucleobases in length targeted to a selected target pre-mRNA, wherein the compound comprises:
   a modified sugar moiety at the 5'-most nucleoside;
   a modified sugar moiety at the 3'-most nucleoside;
   internal nucleosides comprising 2, 3, 4 or 5 separate regions of 2'-deoxyribonucleosides, wherein each region consists of 1, 2, 3 or 4 nucleosides; and
   at least one nucleoside with a modified sugar moiety separating each region of 2'-deoxynucleosides,
   and wherein the chimeric antisense compound has a motif selected from among: 4-3-1-3-1-3-5, 5-3-1-3-1-3-4, 3-2-2-3-2-3-5, 5-3-2-3-2-2-3, 3-3-2-3-2-3-4, 2-3-1-3-1-3-1-3-3, 4-3-2-3-2-3-3, and 2-3-1-3-1-3-1-3-3.

2. The compound of claim 1, wherein the sugar modification is selected from the group consisting of 2'-O-methoxyethyl, 2'-fluoro, 2'-dimethylaminooxyethoxy, 2'-dimethylaminoethoxyethoxy, 2'-guanidinium, 2'-O-guanidinium ethyl, 2'-carbamate, 2'-aminooxy, 2'-acetamido and locked nucleic acid.

3. The compound of claim 2, wherein the sugar modification is 2'-O-methoxyethyl.

4. The compound of claim 2, wherein the sugar modification is locked nucleic acid.

5. The compound of claim 1, wherein the chimeric antisense compound has a 4-3-1-3-1-3-5 motif.

6. The compound of claim 1, wherein the chimeric antisense compound has a 3-2-2-3-2-3-5 motif.

* * * * *